United States Patent
Rice

(10) Patent No.: US 6,573,417 B1
(45) Date of Patent: Jun. 3, 2003

(54) FRACTIONATION OF PARAFFIN ISOMERIZATION PROCESS EFFLUENT

(75) Inventor: Lynn H. Rice, Arlington Heights, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 10/008,991

(22) Filed: Nov. 5, 2001

(51) Int. Cl.[7] .................................................. C07C 5/13
(52) U.S. Cl. ...................... 585/738; 585/734; 585/739; 585/744; 585/747; 585/748
(58) Field of Search ................... 585/734, 738, 585/739, 744, 747, 748

(56) References Cited

U.S. PATENT DOCUMENTS

| | | | |
|---|---|---|---|
| 4,804,803 A | | 2/1989 | Schmidt et al. ............. 585/748 |
| 4,831,209 A | * | 5/1989 | Kruse ......................... 585/738 |
| 5,043,525 A | * | 8/1991 | Haizmann et al. .......... 585/737 |
| 6,416,657 B1 | * | 7/2002 | Fersing et al. .............. 208/141 |

OTHER PUBLICATIONS

*Handbook of Petroleum Refining Processes* 2nd Edition, Robert A. Meyers, editor, McGraw–Hill 1996 Chapters 9.3 and 9.4.
Schmidt, R.J., et al. *Catalyst and Engineering Innovations Improve Isomerization Economics* presented at 1987 National Petroleum Refiners Associated annual meeting, Mar. 29–31, 1987.

* cited by examiner

*Primary Examiner*—Walter D. Griffin
*Assistant Examiner*—Tam M. Nguyen
(74) *Attorney, Agent, or Firm*—John G. Tolomei; Frank S. Molinaro

(57) ABSTRACT

The fractional distillation performed as part of the isomerization of $C_5$–$C_6$ paraffins is heat integrated. A portion of a sidedraw recycle stream is employed to cool the feed to a deisohexanizer column and then returned to a lower portion of the column. This reduces the reflux demand of the column and the operating cost of the process.

4 Claims, 1 Drawing Sheet

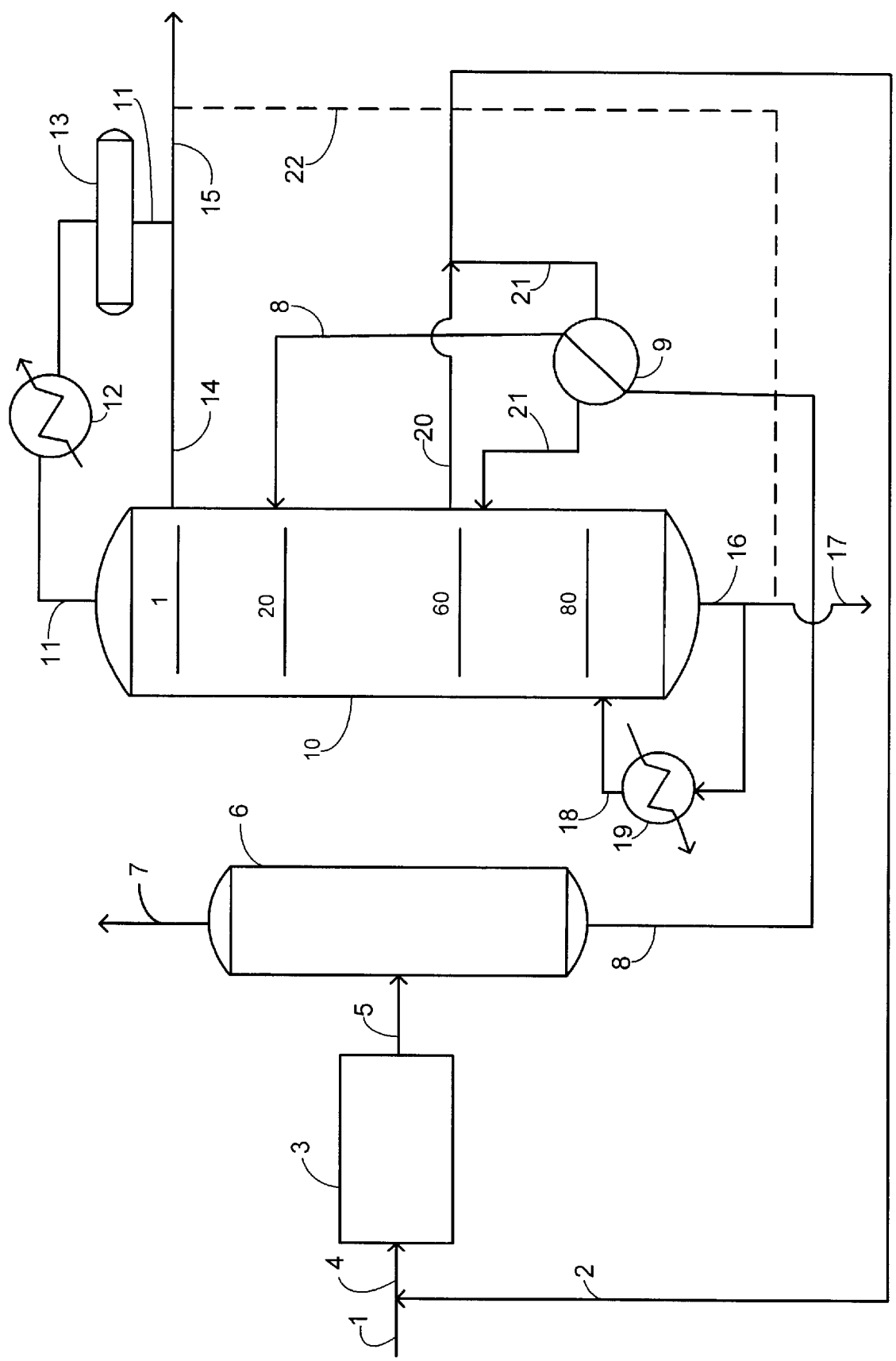

FRACTIONATION OF PARAFFIN ISOMERIZATION PROCESS EFFLUENT

FIELD OF THE INVENTION

The invention relates to a process for the isomerization of a light paraffin feed stream comprising pentanes and hexanes to produce more highly branched paraffins of higher octane number and greater utility as naphtha boiling range motor fuel. The invention specifically relates to an improvement in the heat integration of the fractional distillation scheme used to recover a recycle stream and a product stream from the stabilized effluent stream of an the paraffin isomerization zone.

BACKGROUND OF THE INVENTION

The majority of the naphtha boiling range hydrocarbons recovered from petroleum do not have the high octane numbers desired for modern gasolines. For instance, straight chain or relatively straight chain $C_5$ and $C_6$ hydrocarbons have octane numbers which are much lower than desired for gasoline blending components. As a result it is necessary for modern petroleum refineries to build high octane molecules, as by alkylation, and to increase the octane of existing straight chain molecules by isomerization. By isomerizing these straight chain molecules to more highly branched molecules the octane number of the molecules is increased.

Isomerization of naphtha boiling range hydrocarbons is affected by contacting the hydrocarbons with an isomerization catalyst at isomerization conditions. Unfortunately, such isomerization steps do not result in a complete conversion of the straight chain feed molecules, and a sizable percentage of the isomerate or product of this contacting consists of molecules which have only a moderate increase in branching. In order to further increase the octane number of the isomerization product the higher octane molecules are separated into a product stream while the relatively less branched, and therefore lower octane hydrocarbons, are concentrated into a recycle stream returned to the isomerization zone. Although adsorption is more effective in performing a division between the close boiling low and high octane molecules, it is also more costly. Therefore, this separation step is often performed by fractional distillation. The subject invention relates to fractional distillation steps performed in the recovery of high octane hydrocarbons and the recycling of low octane hydrocarbons to the isomerization zone.

RELATED ART

The isomerization of light paraffins is a well known process performed in many petroleum refineries. As used herein the term "light paraffins" is intended to refer to paraffins having five or six carbon atoms per molecule. An overall description of light paraffin isomerization technology is provided in Chapters 9.3 and 9.4 of the Handbook of Petroleum Refining Processes, second edition, Robert A. Meyers, editor; published in 1996 by McGraw-Hill. These chapters describe processing conditions, catalysts and process flows used in this process. Figure 9.3 illustrates the passage of the reactor effluent into a stabilizer column to recover a product labeled as isomerate. Figure 9.3.2 describes an optional flow in which the effluent of an isomerization reaction zone is passed into a deisohexanizer column which divides the entering material into an isomerate and a recycle stream, which is returned to the isomerization zone. Similar flow schemes with slightly more detail are shown in the paper entitled "Catalyst and Engineering Innovations Improve Isomerization Economics" by R. J. Schmidt, et al., presented at the 1987 National Petroleum Refiners Associated annual meeting on Mar. 29–31, 1987, and in U.S. Pat. No. 4,804,803 issued to R. J. Schmidt et al.

SUMMARY OF THE INVENTION

The invention is an improved configuration of the fractional distillation zone used downstream of a light paraffin isomerization zone. The invention reduces the utility costs of this fractional distillation zone by reducing both the reboiler duty and the amount of cooling required to generate reflux liquid for the top of the column.

A broad embodiment of the invention may be characterized as a process for the isomerization of $C_5$–$C_6$ paraffins and the recovery of high octane, di-branched paraffins by fractional distillation, which process comprises passing a feed stream comprising $C_5$–$C_6$ paraffins into a catalytic reaction zone in which the feed stream is contacted with a paraffin isomerization catalyst maintained at isomerization conditions to yield an isomerization zone effluent stream comprising $C_5$–$C_7$ paraffins; passing the isomerization zone effluent stream into a first fractional distillation column maintained at fractionation conditions effective to remove as an overhead product substantially all hydrocarbons present in the isomerization zone effluent stream having less than 5 carbon atoms per molecule and forming a first net bottoms stream comprising $C_5$–$C_7$ paraffins; cooling the first net bottoms stream by indirect heat exchange against a first process stream; passing the first net bottoms stream into a second fractionation column at an intermediate elevation, with the second fractionation column operated at fractionation conditions effective to separate entering hydrocarbons into a net overhead stream, which is rich in relatively high octane $C_5$ and $C_6$ hydrocarbons including dimethyl butane produced in the isomerization zone, a sidecut stream removed at a lower intermediate elevation of the fractionation column and comprising $C_5$ and $C_6$ normal paraffins, and a net second bottoms stream comprising $C_7$ hydrocarbons; withdrawing a first portion of the sidecut stream; employing a second portion of the sidecut stream as the first process stream referred to above, and, passing the second portion of the sidecut stream into the lower half of the second fractional distillation column at a third intermediate point.

BRIEF DESCRIPTION OF THE DRAWING

The Drawing is a simplified process flow diagram of a light paraffin isomerization process employing a fractionation column (10) to separate the isomerate into a high octane number product (15) and a lower octane recycle stream (2).

DETAILED DESCRIPTION AND PREFERRED EMBODIMENTS

As pointed out above, an isomerization zone can be employed to increase the octane number of the paraffinic hydrocarbons in a naphtha boiling range fraction recovered from petroleum. These paraffinic hydrocarbons, which are separated in the subject process, generally have from 5 to 7 carbon atoms per molecule although some $C_4$ and $C_8$ hydrocarbons may be present due to imprecise prior fractionation. While isomerization processes for broad feeds e.g. $C_4$–$C_6$ are known as from U.S. Pat. No. 5,326,926, the feed to the subject process is preferably substantially free of $C_4$ and $C_8$ hydrocarbons. As used herein the term "substantially"

free" is intended to indicate a concentration of the indicated compound or class of compounds below 5 mol percent. The petroleum-derived fraction will contain a mixture of normal and isoparaffins, with the isoparaffins including mono-, di-, and tri-branched paraffins. It may also contain some coboiling cyclic hydrocarbons. The paraffinic hydrocarbons will range in octane number from low octane straight chain paraffins, such as normal hexane, to high octane more highly branched paraffins, such as dimethyl butane. The octane number of this raw fraction is often fairly low. To upgrade this raw mixture to a higher octane number blending component for use in a modern gasoline, the mixture is charged to an isomerization zone. To achieve the highest possible octane product, the lower octane number components of the isomerization zone effluent are recovered and recycled to the isomerization zone. This can be done to some extent by fractional distillation, which is the lowest cost method of recycling low octane paraffins.

The isomerization technology may also be of conventional nature. The feed and recycle hydrocarbons are contacted with an isomerization catalyst maintained at isomerization conditions preferably in the presence of a limited but positive amount of hydrogen as described in U.S. Pat. Nos. 4,804,803 and 5,326,296. The isomerization catalyst may be amorphous e.g. based upon amorphous alumina, or zeolitic. A zeolitic catalyst would still normally contain an amorphous binder. The catalyst may comprise a sulfated zirconia and platinum as described in U.S. Pat. No. 5,036,035 and European patent application 0 666 109 A1 or a platinum group metal on chlorided alumina as described in U.S. Pat. No. 6,214,764. Another suitable catalyst is described in U.S. Pat. No. 5,922,639. These references are incorporated herein for their teaching as to catalyst compositions, isomerization operating conditions and techniques. Operating temperature of the isomerization zone depends upon the feed composition and catalyst activity. It is usually between about 40 to 160° C. Operating pressure is usually maintained within the range of 2 to 3.5 MPa, with the reactor being operated at an overall L.H.S.V. of about 0.5 to 5 $hr^{-1}$.

The fractionation zone of a light paraffin isomerization process may comprise only a stabilizer, typically a debutanizer. The stabilizer removes light ends, such as hydrogen, low boiling hydrocarbons and chemical additives leaving the isomerate as a bottoms product stream. The product of this once through flow arrangement will have a higher average octane number than the feed stream, but the octane number may be below that desired for use in preparing a modern gasoline product. In this instance it is necessary to separate the relatively low and high octane number molecules present in the stabilizer bottoms stream. The differences in octane number of the hydrocarbons is primarily due to the relative amount of branching of the hydrocarbons, with more highly branched molecules tending to have higher octane numbers. It is possible to perform a rough division into relatively high and low octane hydrocarbons by fractional distillation, which makes it possible to recycle many of the unconverted lower octane straight chain and mono-branched hydrocarbons to the isomerization zone. The fractionation column employed to perform this separation is referred to as a deisohexanizer. The fractionation system of the isomerization zone therefore becomes a sequence of a stabilizer followed by a deisohexanizer.

In the conventional flow of this sequence of columns the bottoms stream of the stabilizer is passed directly into the deisohexanizer. It has now been found that this can be improved by the subject process. In the conventional flow the bottoms stream of the stabilizer is hotter than the contents of the deisohexanizer column at the point at which the bottoms stream is charged to the deisohexanizer. As a result the bottoms stream "overflashes" upon entry into the deisohexanizer. This is compensated for by supplying a high rate of reflux to the top of the column. In the subject invention the unneeded heat in the stabilizer bottoms stream is removed from the bottoms stream and employed at a lower level in the column where more heat is needed. This is performed by indirect heat exchange of a portion of a sidedraw stream against the bottoms stream. While a stabbed-in heat exchanger could be employed between the feed point and the side draw to recover this heat, that approach would make it necessary to increase the size of the deisohexanizer in order to accommodate the heat exchanger. The invention solves this problem by transferring the heat to a portion of the sidedraw and then returning this portion of the sidedraw to a point near the sidedraw withdrawal point to help reboil the column. A further advantage of employing a heat exchanger located outside of the column rather than a stabbed-in heat exchanger is that this allows the reboiler to be located at or close to ground level, where maintenance is much easier. However, the primary benefit of the invention is a reduction in utility costs. The heat recovered from the stabilizer bottoms is used to partially reboil the deisohexanizer, and by eliminating the overflash of the column feed stream the required amount of reflux is reduced. Therefore both the heat and cooling duty of the deisohexanizer is reduced.

Referring now to the drawing, there is shown a simplified flow diagram of an isomerization process employing the subject invention. A feed stream comprising mainly a mixture of $C_5$ and $C_6$ hydrocarbons but contaminated with small amounts of $C_4$ and $C_7$ hydrocarbons is passed into the process through line 1. This entering feed stream is admixed with a recycle stream from line 2. The recycle stream comprises normal paraffins and other relatively low octane $C_5$ and $C_6$ hydrocarbons. The combined feed stream is then passed through line 4 into the isomerization zone 3. The isomerization zone will contain one or more reactors in a reaction zone, charge heaters, heat exchangers, and conventional accessory apparatus, such as for the addition and recovery of hydrogen. In the isomerization zone 3 the entering combined feed stream is brought up to reaction conditions including an elevated temperature and pressure and brought into contact with one or more isomerization catalysts. This effects the conversion of a portion of the entering straight chain paraffins to branched paraffins and also a partial conversion of mono-branched low octane molecules, such as those containing a single methyl group, into higher octane number, more highly branched hydrocarbons. This conversion, however, is incomplete and the effluent stream of the isomerization reaction zone 3 will comprise a mixture of normal paraffins, mono-branched paraffins and multi-branched paraffins. The carbon number range of these paraffins is basically set by the carbon number range of the feed stream of line 1. It will be predominantly $C_5$ and $C_6$ hydrocarbons.

The effluent of the isomerization zone is passed via line 5 into a stripping or stabilizing column 6. The representation of this column is simplified by the deletion of normally provided overhead condensation and lower reboiling systems. The stripping column 6 is operated at conditions and designed to effect a separation of dissolved hydrogen and light hydrocarbons, such as butane and propane, into a net overhead vapor stream removed in line 7. These light hydrocarbons may be formed as reaction byproducts or may have been present in small amounts in the feed stream of line 1 due to the imprecise fractional distillation of the feed stream. The net overhead stream of line 7 may also comprise volatile chemical compounds, typically chlorides, which were added to the isomerization zone for the maintenance of catalyst activity. The net overhead gas is directed to appropriate treatment and recovery facilities of conventional nature.

The stripping or stabilization column 6 produces a net bottoms stream removed through line 8. This net bottoms stream comprises unconverted $C_5$ and $C_6$ hydrocarbons from the feed and recycle streams plus the converted hydrocarbons. The net bottoms stream is first cooled in the external heat exchanger 9 and then passed through line 8 to an upper intermediate portion of the deisohexanizer column 10. As used herein, the term intermediate point is intended to indicate a point in a fractionation column which is separated from the top and bottom of the column by vapor-liquid contacting media e.g. trays providing a separation capacity equal to at least three theoretical stages of contacting. A representative feed point into the deisohexanizer column 10 is tray number 20 as illustrated in the drawing. Only those trays which are indicative of appropriate levels in the column are illustrated and labeled. The column 10 preferably contains fractional distillation trays but may also contain other vapor-liquid contacting means including packing. It is designed and operated to separate the entering hydrocarbons into at least three fractions. The lightest of these three fractions is the net overhead stream recovered through line 15. The net overhead stream is produced by condensation of the overhead vapor which is removed through line 11 and condensed in heat exchanger 12. The condensate is collected in the overhead receiver 13, and the liquid is withdrawn through line 11. The overhead condensate is then divided into the net overhead product of line 15 and a stream returned to tray number 1 as reflux via line 14.

At the bottom of the deisohexanizer column 10 a bottoms stream is removed through line 16 and divided into a first portion removed as the net bottoms product of line 17 and a second portion passed through line 18. The liquid flowing through line 18 is heated in the reboiler 19 and returned to a bottom portion of the column near tray number 80 to effect the addition of heat energy and vapor generation in the column. An optional line 22 is shown on the drawing to indicate all or a portion of the net bottoms stream may be passed through this line and blended into the net overhead product stream of line 15.

At a lower intermediate point, equal in this instance to the level of tray number 60, a side stream is removed. This side stream may be removed as a liquid phase stream collected in a trap-out tray or by other liquid collection means. The sidecut stream is removed in line 20 and divided into a first portion which becomes the recycle stream of line 2 returned to the isomerization zone 3 and a second portion carried by line 21. The second portion of the sidecut stream passes through the heat exchanger 9 and cools the feed to the deisohexanizer column. This second portion of the sidedraw stream is heated in this exchange. It is passed into a point in the lower half of the deisohexanizer column 10. This point is preferably within five actual trays of the point at which the side steam is removed. It may be either above or below this point. The preferred location may change with process conditions and stream compositions.

The table below sets out the octane numbers, both research octane (RON-C) and motor octane (MON-C) of some representative components of a $C_5$–$C_6$ motor fuel isomerate. This information is presented to show the range between such low octane materials as n-pentane and n-hexane and high octane materials, such as the dimethyl butanes. The mono-branched materials have an intermediate octane. As used herein the term high octane is intended to indicate an octane number (R&M/2) by ASTM methods greater than 86. Low octane is similarly defined as less than 80.

|  | ASTM | |
|---|---|---|
|  | RON-C | MON-C |
| $C_5$: | | |
| i-Pentane | 92.3 | 90.3 |
| n-Pentane | 61.7 | 62.6 |
| $C_6$: | | |
| 2,2-Dimethylbutane | 91.8 | 93.4 |
| 2,3-Dimethylbutane | 103.5 | 94.3 |
| 2-Methylpentane | 73.4 | 73.5 |
| 3-Methylpentane | 74.5 | 74.3 |
| n-Hexane | 24.8 | 26.0 |
| Methylcyclopentane | 91.3 | 80.0 |
| Cyclohexane | 83.0 | 77.2 |
| Benzene | 120.0 | 115.0 |

The following is non-limiting illustrative example based upon engineering calculations and operational experience for light paraffin isomerization units and fractionation columns used in the separation and recovery of the effluent of these isomerization units. The example is based upon a $C_5$–$C_6$ feed stream having a flow rate of 121,252 lbs/hr. containing about 40 mol. percent normal paraffins and about 40 mol. percent branched paraffins. The feed stream contains about 5% dimethylbutane. The example follows the flow scheme shown in the drawing.

The effluent of the reaction zone (line 5) is about 241,066 lbs/hr. It is passed into the debutanizer column 6 which produces a net overhead product of 2,851 lbs/hr. The net bottoms stream of the debutanizer is withdrawn at a temperature of 201° C. (394° F.). It is cooled to 123° C. (253° F.) in heat exchanger 9 and then charged onto the twentieth tray of the deisohexanizer 10. The overhead vapor is removed at 77° C. (171° F.) and about 19 psig and is passed through the condenser 12. A net overhead stream is removed at a rate of 103,669 lbs/hr. at 65° C. (149° F.), and a reflux stream of 389,712 lbs/hr. is passed onto the top tray of the deisohexanizer. The net overhead stream contains about 50 percent dimethylbutane and about 5 percent normal paraffins. A bottoms stream having temperature of about 141° C. (286° F.) is removed via line 16 and divided into the reboiler feed and net bottoms stream. The net bottoms stream has a flow rate of about 2,228 lbs/hr. and contains about 95 percent $C_7$ hydrocarbons.

A sidecut stream is removed from the sixtieth tray of the deisohexanizer and divided into recycle stream of line 2 and the process stream of line 21. The recycle stream has a flow rate of about 118,285 lbs/hr. and contains 25% n-paraffins. About 85% of this stream is $C_6$ hydrocarbons with essentially no (less than 0.1 percent) $C_5$ hydrocarbons being present. The process stream of line 21 is heated to about 111° C. (232° F.) in the heat exchanger and then passed into the deisohexanizer column under tray 60 of the column.

What is claimed:
1. A process for the isomerization of $C_5$–$C_6$ paraffins and the recovery of high octane, di-branched paraffins by fractional distillation, which process comprises:
   a.) passing a feed stream comprising $C_5$–$C_6$ paraffins into a catalytic reaction zone in which the feed stream is contacted with a paraffin isomerization catalyst main- tained at isomerization conditions to yield an isomerization zone effluent stream comprising $C_5$–$C_7$ paraffins;

b.) passing the isomerization zone effluent stream into a first fractional distillation column maintained at fractionation conditions effective to yield as an overhead product substantially all hydrocarbons present in the isomerization zone effluent stream having less than 5 carbon atoms per molecule and forming a first net bottoms stream comprising $C_5$–$C_7$ paraffins;

c.) cooling the first net bottoms stream by indirect heat exchange against a first process stream;

d.) passing the first net bottoms stream into a second fractionation column at an intermediate elevation, with the second fractionation column operated at fractionation conditions effective to separate entering hydrocarbons into a net overhead stream, which is rich in relatively high octane $C_5$ and $C_6$ hydrocarbons including dimethyl butane produced in the isomerization zone, a sidecut stream removed at a lower intermediate elevation of the fractionation column and comprising methyl pentanes and $C_6$ normal paraffins, and a second net bottoms stream comprising $C_7$ hydrocarbons;

e.) withdrawing a first portion of the sidecut stream;

f.) employing a second portion of the sidecut stream as the first process stream referred to in step c): and g.) passing the second portion of the sidecut stream into the lower half of the second fractional distillation column at a third intermediate point.

2. The process of claim 1 further characterized in that the second portion of the sidecut stream is passed into the second fractional distillation column at a point within five actual trays of the lower intermediate point at which the sidecut stream is removed.

3. A process for the isomerization of $C_5$–$C_6$ paraffins and the recovery of high octane, di-branched paraffins by fractional distillation, which process comprises:

a.) passing a feed stream comprising $C_5$–$C_6$ paraffins into a catalytic reaction zone in which the feed stream is contacted with a paraffin isomerization catalyst maintained at isomerization conditions to yield an isomerization zone effluent stream comprising $C_5$–$C_7$ branched paraffins;

b.) passing the isomerization zone effluent stream into a first fractional distillation column maintained at fractionation conditions effective to remove as an overhead product substantially all hydrocarbons present in the isomerization zone effluent stream having less than 5 carbon atoms per molecule and forming a first net bottoms stream comprising $C_5$–$C_7$ paraffins;

c.) cooling the first net bottoms stream by indirect heat exchange against a first process stream;

d.) passing the first net bottoms stream into a second fractionation column at an intermediate elevation, with the second fractionation column operated at fractionation conditions effective to separate entering hydrocarbons into a net overhead stream, which is rich in relatively high octane $C_5$ and $C_6$ hydrocarbons including dimethyl butane produced in the isomerization zone, a sidecut stream removed at a lower intermediate elevation of the fractionation column and comprising $C_5$ and $C_6$ normal paraffins, and a second net bottoms stream comprising $C_7$ hydrocarbons;

e.) passing a first portion of the sidecut stream into the catalytic reaction zone;

f.) employing a second portion of the sidecut stream as the first process stream referred to in step c): and g.) passing the second portion of the sidecut stream into the second fractional distillation column at a third intermediate point which is lower than the lower intermediate elevation.

4. The process of claim 3 further characterized in that the second net bottoms stream is blended into the net overhead stream of the second fractionation column.

* * * * *